(12) United States Patent
Rump

(10) Patent No.: US 10,617,865 B2
(45) Date of Patent: Apr. 14, 2020

(54) ELECTRODE EXTENSION INTEGRATED IN AN ACTIVE IMPLANT

(71) Applicant: BIOTRONIK SE & CO. KG, Berlin (DE)

(72) Inventor: Jens Rump, Berlin (DE)

(73) Assignee: BIOTRONIK SE & CO. KG, Berlin (DE)

( * ) Notice: Subject to any disclaimer, the term of this patent is extended or adjusted under 35 U.S.C. 154(b) by 1132 days.

(21) Appl. No.: 14/946,617

(22) Filed: Nov. 19, 2015

(65) Prior Publication Data

US 2016/0151625 A1 Jun. 2, 2016

Related U.S. Application Data

(60) Provisional application No. 62/085,249, filed on Nov. 27, 2014.

(51) Int. Cl.

| A61N 1/08 | (2006.01) |
|---|---|
| A61N 1/37 | (2006.01) |
| A61B 5/042 | (2006.01) |
| A61N 1/05 | (2006.01) |
| A61N 1/362 | (2006.01) |
| A61N 1/39 | (2006.01) |
| A61N 1/375 | (2006.01) |

(52) U.S. Cl.
CPC .............. *A61N 1/08* (2013.01); *A61B 5/042* (2013.01); *A61N 1/05* (2013.01); *A61N 1/362* (2013.01); *A61N 1/3718* (2013.01); *A61N 1/3956* (2013.01); *A61N 1/086* (2017.08); *A61N 1/3754* (2013.01)

(58) Field of Classification Search
CPC ........ A61B 5/042; A61N 1/05; A61N 1/0585; A61N 1/0587; A61N 1/08; A61N 1/086; A61N 1/3752; A61N 1/3754; A61N 1/3756

See application file for complete search history.

(56) References Cited

U.S. PATENT DOCUMENTS

| 2003/0144718 A1* | 7/2003 | Zeijlemaker ........... A61N 1/056 607/122 |
| 2005/0154428 A1* | 7/2005 | Bruinsma ................ A61N 1/40 607/60 |
| 2009/0243756 A1* | 10/2009 | Stevenson ............ H03H 7/1766 333/172 |

(Continued)

*Primary Examiner* — Eun Hwa Kim
(74) *Attorney, Agent, or Firm* — Arc IP Law, PC; Joseph J. Mayo

(57) ABSTRACT

Embodiments include a temporarily or permanently implantable medical device, wherein the medical device includes a housing connected to at least one elongate electrical function conductor to transmit therapy signals or diagnosis signals or both. The medical device includes at least one electrode pole connected to the at least one elongate electrical function conductor, via which electrode pole electric current is delivered to adjacent bodily, or electrode pole electrical potentials are sensed in surrounding tissue, or both. The medical device includes, in the housing, an electrical component as a line extension, wherein the electrical component is connected to the at least one elongate electrical function conductor and includes an electric length that is at least a quarter of a wavelength λ (lambda) of electromagnetic waves in a radio frequency range, such as of MRI scanners.

11 Claims, 5 Drawing Sheets

(56) References Cited

U.S. PATENT DOCUMENTS

| | | | |
|---|---|---|---|
| 2010/0174348 A1* | 7/2010 | Bulkes | A61N 1/05 607/116 |
| 2010/0331917 A1* | 12/2010 | DiGiore | A61N 1/08 607/61 |
| 2011/0009754 A1* | 1/2011 | Wenzel | A61B 5/0215 600/485 |
| 2012/0109002 A1* | 5/2012 | Mothilal | A61B 5/0215 600/549 |
| 2012/0109261 A1* | 5/2012 | Stancer | A61N 1/025 607/60 |
| 2012/0171981 A1* | 7/2012 | Hiers | H10Q 13/0275 455/334 |
| 2013/0338747 A1* | 12/2013 | Kondabatni | A61N 1/05 607/116 |

* cited by examiner

ELECTRODE EXTENSION INTEGRATED IN AN ACTIVE IMPLANT

This application claims the benefit of U.S. Provisional Patent Application 62/085,249 filed on 27 Nov. 2014, the specification of which is hereby incorporated herein by reference.

BACKGROUND OF THE INVENTION

1. Field of the Invention

Embodiments of the invention generally relate to a permanently or temporarily implantable device used with an elongate electrical conductor.

2. Description of the Related Art

Generally, elongate electrical conductors are contained for example in electrode lines for electrostimulation. Typically, such electrode lines have the disadvantage that the electrical conductor thereof may heat up in an MRI scanner, because the alternating magnetic fields prevailing in the MRI scanner induce electric currents in the electrical conductor that are significant. Generally, such induced currents may also be delivered via electrode poles of the electrode line to surrounding tissue and for example may thus lead to undesirable heating of the tissue. Therefore, typically, cardiac pacemaker patients nowadays generally cannot be examined in a magnetic resonance imaging (MRI) scanner or may only be examined in this way to a limited extent.

Specifically, at least one stimulation electrode line is typically connected to implantable cardiac pacemakers or defibrillators, also referred to hereinafter as heart stimulators or implantable pulse generators (IPGs). Generally, at its proximal end intended for connection to the cardiac pacemaker or defibrillator, the stimulation electrode line includes a standardized electrical terminal, and, at its distal end intended for placement in the heart, includes one or more electrode poles. Such an electrode pole is typically used to deliver electrical pulses to the tissue (myocardium) of the heart or to sense electrical fields in order to sense cardiac activity, also referred to as sensing. For this purpose, electrode poles typically form electrically conductive surface portions of an electrode line. Electrode poles are typically provided as ring electrodes in the form of a ring around the electrode line or in the form of a point electrode or tip electrode at the distal end of the electrode line. The electrode poles are generally electrically conductively connected via one or more electrical conductors to contacts of the electrical terminal of the electrode line at the proximal end thereof. One or more electrical conductors, which electrically connect one or more of the electrode poles to one or more of the contacts, thus typically run between the contacts of the electrical terminal of the electrode lines at the proximal ends thereof and the electrode poles at the distal end of the electrode line. These electrical conductors, generally, may be used on the one hand for transmission of stimulation pulses to the electrode poles and on the other hand for transmission of electrical signals, received by means of the electrode poles, to the proximal end of the electrode line, also be referred to herein as function conductors or function lines. Such function lines are typically electrical conductors necessary for the functions of the respective electrode line and as such are exposed to the risk that electrical currents are induced therein as a result of external alternating magnetic fields. The electrical currents for example may typically lead to an undesirable heating of the function conductors or of the electrode poles connected thereto, or may lead to the delivery of corresponding currents via the electrode poles to surrounding tissue and therefore to a heating of the surrounding tissue.

BRIEF SUMMARY OF THE INVENTION

One or more embodiments of the invention include a device that overcomes the previously described problems discussed above with known devices.

At least one embodiment of the invention includes a temporarily or permanently implantable medical device that includes a housing, wherein the housing may be connected to at least one elongate electrical function conductor to transmit therapy signals or diagnosis signals or both. In one or more embodiments, the implantable medical device may include at least one electrode pole connected to the at least one elongate electrical function conductor. In at least one embodiment, electric current may be delivered to adjacent body tissue or electrical potentials may be sensed in surrounding tissue during use, or both, via the at least one electrode pole.

In at least one embodiment of the invention, the housing of the implantable medical device may include an electrical component, such as a line extension, which may be connected to the at least one elongate electrical function conductor. In one or more embodiments, the electrical component may include an electric length that is at least a quarter of the wavelength λ (lambda) of electromagnetic waves in a radio frequency range, such as in MRI scanners.

By way of at least one embodiment, the extension of the electrode line within the housing of the implantable medical device may cause a reduction of undesirable radio frequency (RF) induced heating, without fundamental modifications of the design of the electrode line. In one or more embodiments, the proximal portion, which may be sensitive to RF induced heating, of the electrode line may be shielded by the housing of the implantable medical device, such as a pacemaker. As such, in at least one embodiment, the effect thereof is independent of the frequency of an irradiated wave and is therefore effective for both 1.5 tesla and for 3 tesla magnetic fields during MRI.

At least one embodiment of the invention may include extending the feed line within the housing of the implantable medical device, such that the energy coupled in at the proximal end of the electrode line may be reduced and such that an amplitude of electromagnetic waves is minimal at the point at which electrical signals, for example stimulation or sensing signals, are decoupled at a distal end of the electrode line.

In one or more embodiments, the implantable medical device may include a heart stimulator with an electrode line, in which the function conductors may include electrical conductors of the electrode line, and wherein the electrode line may include electrode poles electrically connected via the function conductors to a wave transfer module.

In at least one embodiment, disadvantages of known devices, including use of band-stop filters, low-pass filters, shunts, billabongs or spur lines, may be avoided by the use of the line extension as presented herein. Such disadvantages of known devices, for example, typically include wherein filter elements are integrated into the electrode body. As such, generally, with known devices, various design concepts may not be used, such that a deviation from optimal electrode design is inevitably necessary.

Typically, with known devices, the design is weakened in terms of the physiological properties thereof. For example, with known devices, the electrode is generally larger and more rigid, such that the risk of tissue irritation and perforation rises. In addition, typically, filter elements are located in the therapeutic path. As such, the longevity of the electrode structure is generally "endangered" or restricted, wherein band-stop filters are typically frequency-selective.

In at least one embodiment of the invention, the housing, for example of an implantable heart stimulator connected to an electrode line, may be conductive or may include an electrode pole, via which, during use, electric current may be delivered to surrounding body tissue or electrical potentials may be sensed in surrounding tissue, or both electric current may be delivered to surrounding body tissue and electrical potentials may be sensed in surrounding tissue.

In one or more embodiments, the implantable medical device may include an impedance matching component that impedance matches between the function conductor and the at least one electrical component, such as a line extension with the electric length $>\lambda/4$. In at least one embodiment, the impedance matching component may detect a presence of strong electromagnetic fields, and, when detected, the impedance matching component may generate a corresponding output signal in order to initiate damping.

In one or more embodiments, the impedance matching component may be a spur line or may include a spur line.

In at least one embodiment, the impedance matching component may be a balun or may include a balun.

In at least one embodiment, the impedance matching component may be a capacitor or may include a capacitor.

In one or more embodiments, the impedance matching component may be an inductor or may include an inductor.

According to at least one embodiment, the impedance matching component may be a combination of an inductor and a capacitor or may include a combination of an inductor and a capacitor.

By way of one or more embodiments, the at least one electrical component, of which the electric length corresponds to at least a quarter of the wavelength $\lambda$ of electromagnetic waves in the radio frequency range, such as the line extension, may be insulated along a length thereof.

In at least one embodiment, the electrical component, of which the electric length corresponds to at least a quarter of the wavelength $\lambda$ of electromagnetic waves in the radio frequency range, may be in contact with a medium that entirely or partially includes one or more of glass, barium titanate, polyethylene, silicon oxide, silicon carbide, ceramic, piezo materials, alumina, titanium oxide, tantalum oxide, semiconductor materials, and plastics.

In one or more embodiments, the electrical component, of which the electric length corresponds to at least a quarter of the wavelength $\lambda$ of electromagnetic waves in the radio frequency range, may include an extension conductor. In at least one embodiment, the extension conductor may include one or more of a wire/band, a platinum-plated wire/band, a wound wire/band, a stranded wire, a cable, a printed conductor, a cut conductor, an etched conductor, a galvanically deposited conductor, and a slitted conductive surface.

In at least one embodiment of the invention, the implantable medical device may include a battery-operated electronic implant with an electrically conductive housing or a housing with at least one electrode pole, and electrical function conductors. In one or more embodiments, the electrical function conductors may connect electrode poles via electric feedthroughs of the implant to convey electrical signals from the respective electrode pole into the implant.

BRIEF DESCRIPTION OF THE DRAWINGS

The above and other aspects, features and advantages of at least one embodiment of the invention will be more apparent from the following more particular description thereof, presented in conjunction with the following drawings, wherein.

DETAILED DESCRIPTION OF THE INVENTION

The following description is of the best mode presently contemplated for carrying out at least one embodiment of the invention. This description is not to be taken in a limiting sense, but is made merely for the purpose of describing the general principles of the invention. The scope of the invention should be determined with reference to the claims.

Figure 1:
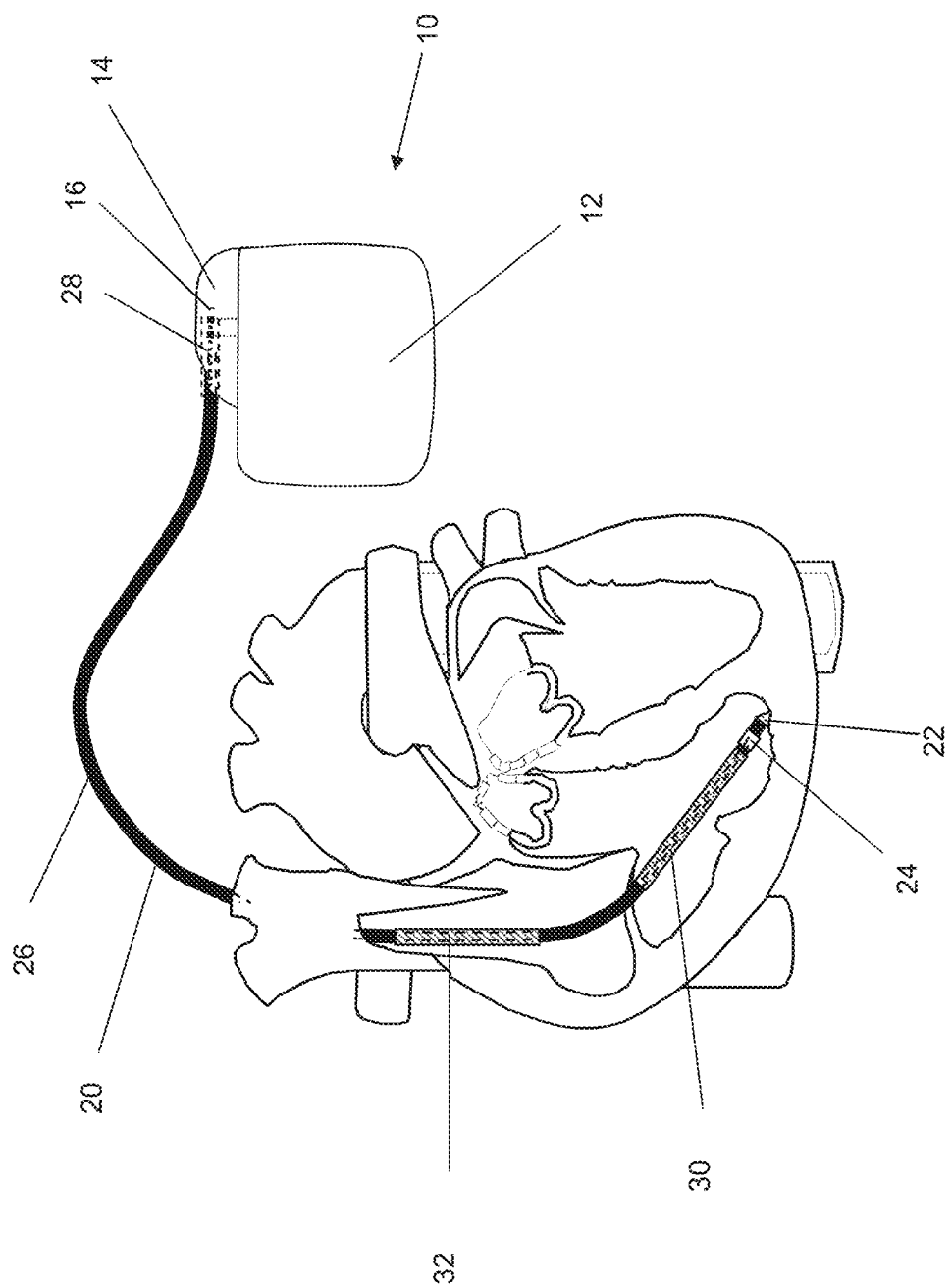
FIG. 1 shows an implantable medical device, such as an implantable heart stimulator, and an implantable electrode line connected thereto.
Figure 4:
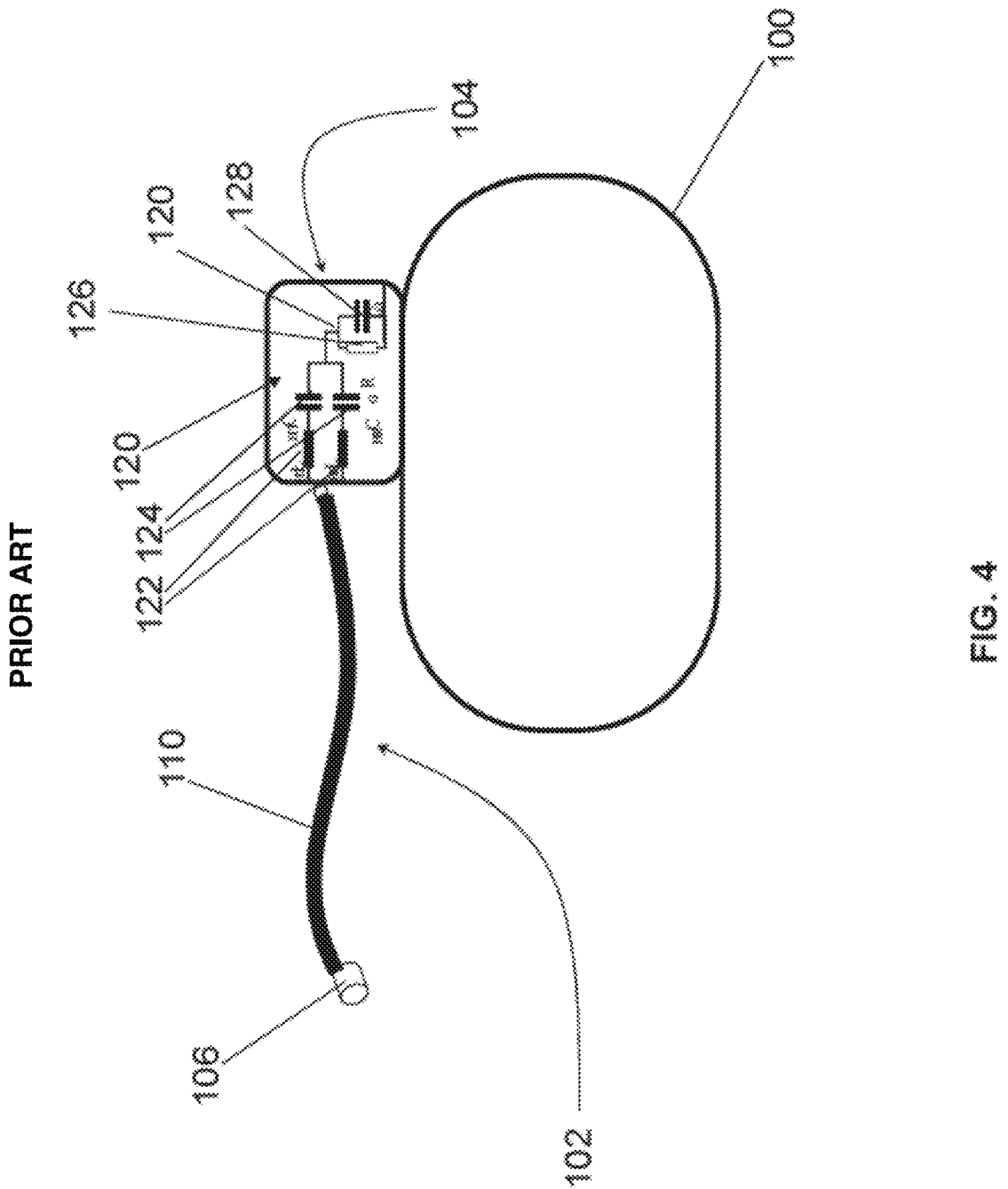
FIG. 4 shows, in a schematic illustration, a prior art device of a heart stimulator with a filter feedthrough.
Figure 5:
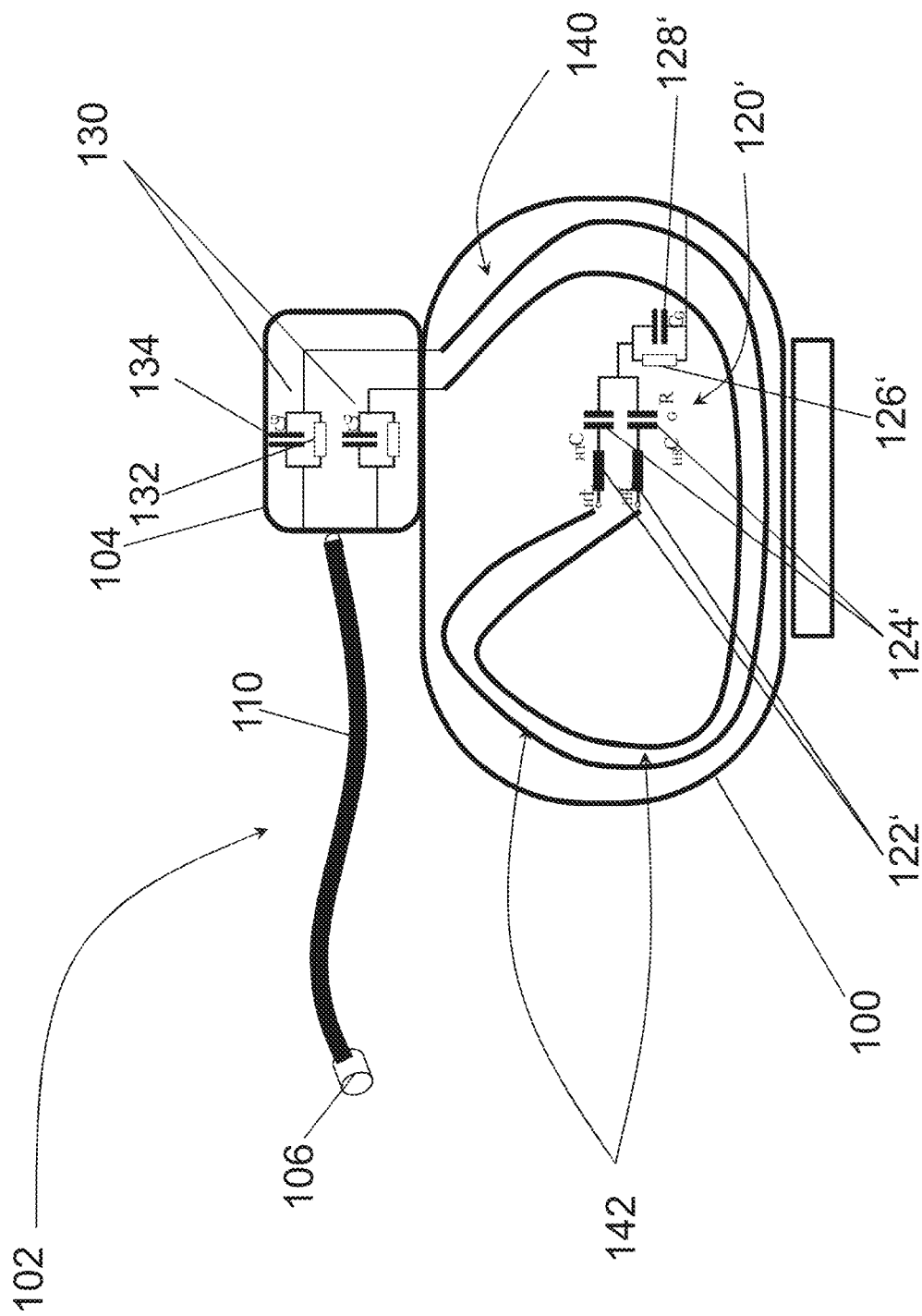
FIG. 5 shows, in a schematic illustration, a heart stimulator with a line extension, according to one or more embodiments of the invention.

FIG. 1 shows an implantable medical device, for example an active implantable medical device, such as an implantable heart stimulator 10, according to one or more embodiments of the invention. Details of the implantable medical device, according to at least one embodiment of the invention, are illustrated in FIGS. 4 and 5 as will be discussed further below.

In one or more embodiments, the implantable medical device, or implantable heart stimulator 10, may be a cardiac pacemaker or a cardioverter/defibrillator (ICD). In at least one embodiment, the heart stimulator 10 may be a ventricular cardiac pacemaker and defibrillator. In one or more embodiments, the implantable heart stimulator may include a dual-chamber cardiac pacemaker to stimulate a right atrium and a right ventricle, or a biventricular cardiac pacemaker that may stimulate the left ventricle and the right ventricle.

By way of at least one embodiment, the implantable heart stimulator 10 may include a housing 12, wherein the housing 12 consists of or includes metal such that the housing is electrically conductive and may serve as a large-area electrode pole. At least one embodiment of the invention may include a terminal housing 14, also referred to as a header, fastened to an outer face of the housing 12. In one or more embodiments, the header may include contact sockets that receive plug contacts. In at least one embodiment, the contact sockets may include electrical contacts 16 connected via corresponding conductors to an electronics unit located in the housing 12 of the heart stimulator 10.

In one or more embodiments of the invention, the electrode line 20 constitutes an implantable medical device. At least one embodiment of the invention may include electrode poles at the distal end of the electrode line 20. In one or more embodiments the electrode poles include a point electrode or tip electrode 22 and a ring electrode 24 arranged in the vicinity of the tip electrode or point electrode 22. In one or more embodiments, the electrode poles 22 and 24 may, depending on the function of a heart stimulator to which the electrode line 20 is connected, be used to sense electrical potentials of the heart tissue (myocardium) or to deliver electrical signals, for example to deliver stimulation pulses to the surrounding heart tissue. FIG. 1 shows how the electrode poles, such as the tip electrode 22 and the ring electrode 24, are located in an apex of a right ventricle of a heart with the electrode line 20, according to one or more embodiments of the invention.

In at least one embodiment, both the tip electrode 22 and the ring electrode 24 may be electrically connected via at least one electrical conductor 26 to a plug contact 28 at the proximal end of the electrode line 20. In one or more embodiments, the plug contact 28 may include electrical contacts that correspond to the electrical contacts 16 of the contact socket in the terminal housing 14 of the implantable heart stimulator. In at least one embodiment, the electrical conductors 26 in the electrode line 20 may be formed as approximately elongate cable conductors or as helically wound conductors. Such conductors, in one or more embodiments, which electrically conductively connect functional electrode poles to electrical contacts of the plug contact at the proximal end of the electrode line 20, are also referred to herein as function conductors. In at least one embodiment, the function conductors may transmit electrical signals, to apply therapy, from the plug contact to the respective electrode pole. In one or more embodiments, the function conductors may transmit sensed signals representing electrical potentials from the respective electrode pole to the plug contact. As such, in at least one embodiment, the function conductors may be used during basic function of the medical device.

In one or more embodiments, the electrical conductors 26, which connect the electrode poles 22 and 24 to the electrical contacts of the plug 28 of the electrode line 20, may be surrounded over the majority of a length thereof by an insulating sleeve, such that electrical contact with the tissue of the heart is produced selectively via the electrode poles.

By way of at least one embodiment, in addition to or alternatively to the electrode poles 22 and 24, which may be used to stimulate the heart tissue such as by ventricular stimulation, the electrode line 20 may include two electrode poles 30 and 32. In one or more embodiments, the electrode poles 30 and 32 may include a greater area than the electrode poles 22 and 24, may be used as defibrillation electrodes and may be formed by or include at least one bare helically wound wire.

It should be noted wherein one or more embodiments are explained within the scope of the invention on the basis of a right-ventricular cardiac pacemaker and defibrillator. However, at least one embodiment of the invention may include an ablation electrode line, for example, as the medical device, wherein the ablation electrode line, in the event of use, may protrude into the heart of a patient, and may be controlled by a device arranged outside of the patient and be connected thereto.

Figure 2:
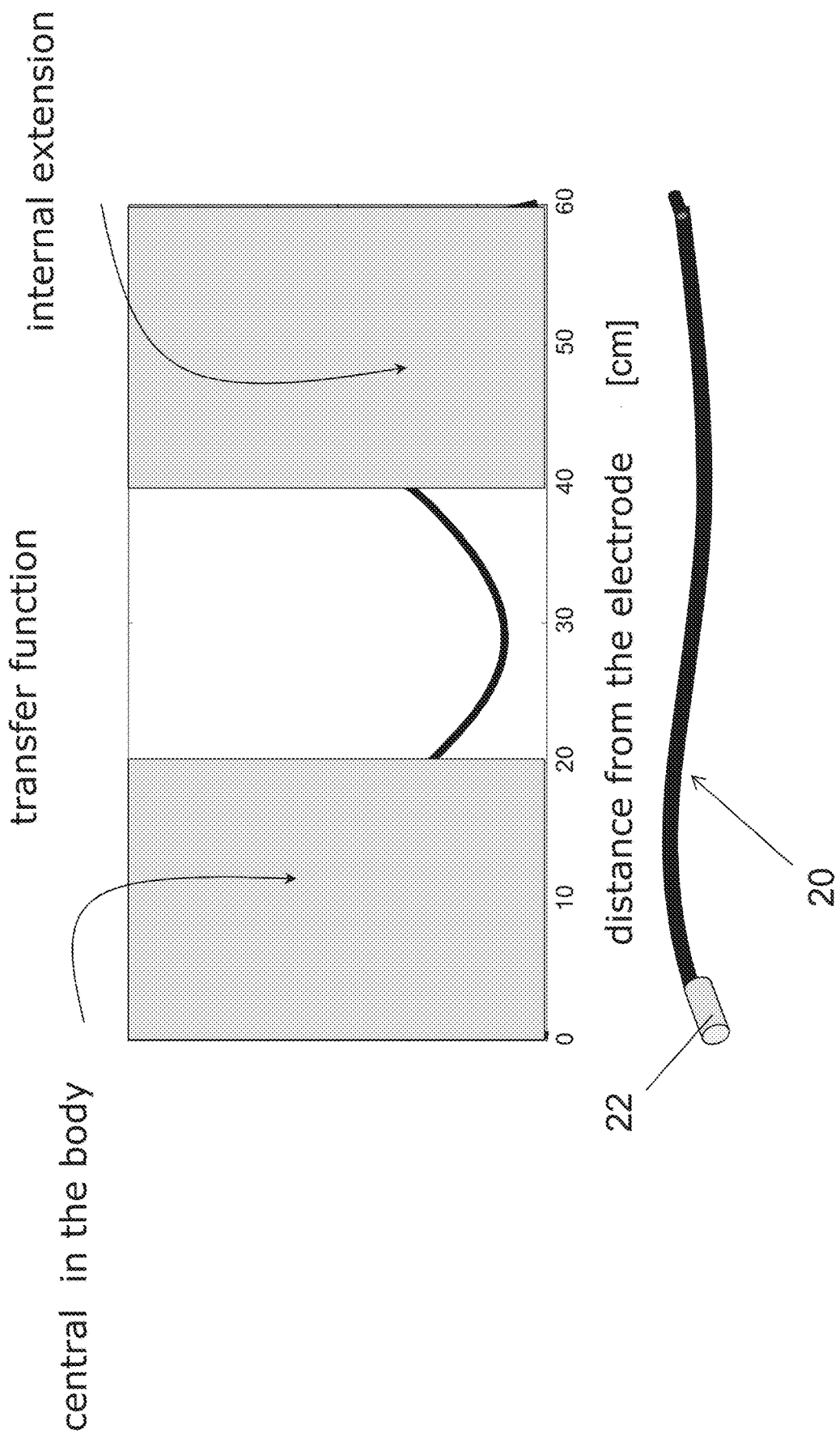
FIG. 2 illustrates a superposition of electromagnetic waves in an electrode line.
Figure 3:
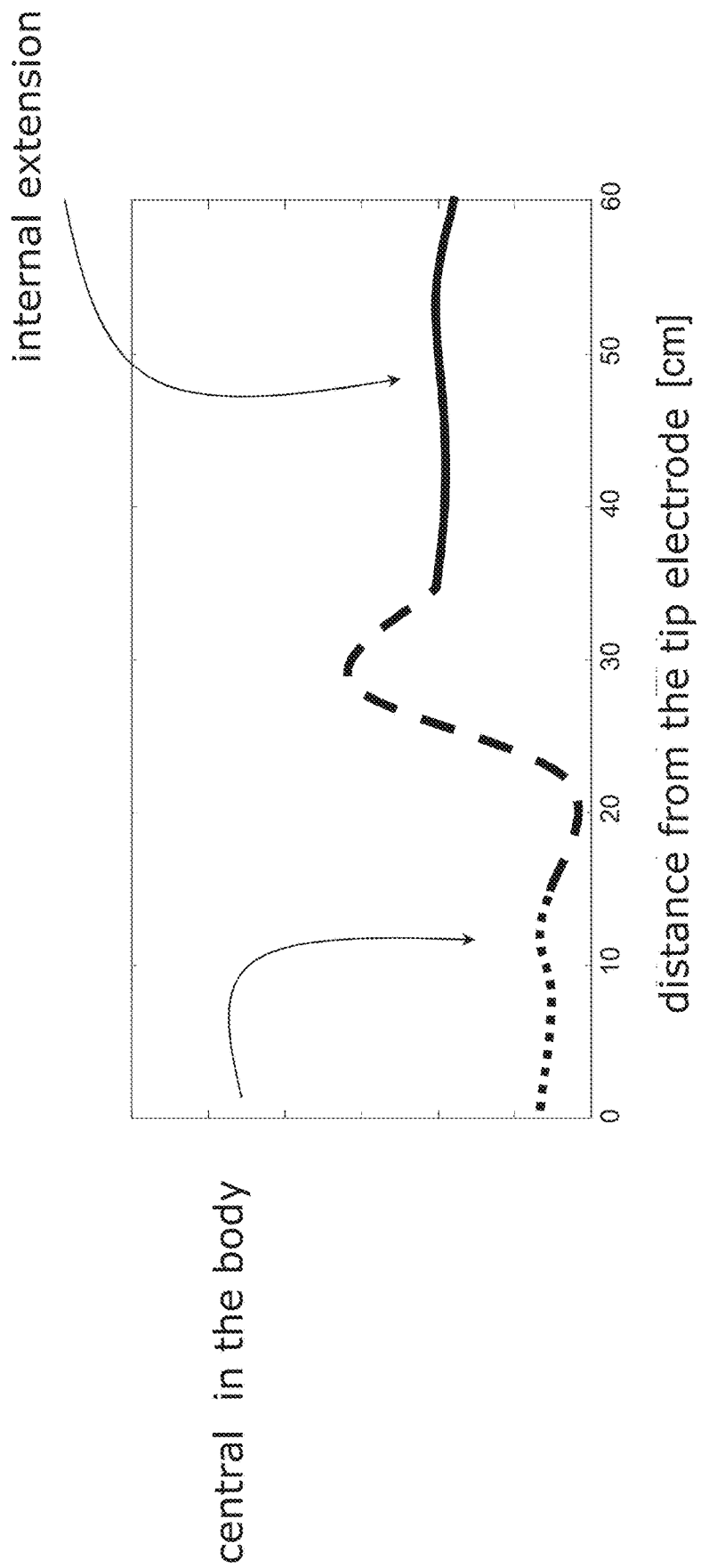
FIG. 3 illustrates amplitudes of external alternating magnetic fields along implanted electrode lines.

FIGS. 2 and 3 illustrate how an external electromagnetic field may lead to a heating of body tissue in the vicinity of the distal end of an electrode line such as the electrode line 20, according to one or more embodiments of the invention. FIG. 2 illustrates a superposition of electromagnetic waves in an electrode line, and FIG. 3 illustrates amplitudes of external alternating magnetic fields along implanted electrode lines, according to one or more embodiments of the invention.

In at least one embodiment, a superposition principle of elementary waves along a conductor may apply to the coupling of electromagnetic waves into elongate electrical conductors such as the conductor 26 of the electrode line 20. In one or more embodiments, the amplitude of the decoupling results from a constructive or destructive superposition of the waves at a location of the decoupling. By way of at least one embodiment, implantable conductors may be heavily damped, and as such, with regard to the coupling-in of electromagnetic waves at the end of the electrical conductor, a coupling-in in the vicinity of both ends of the electrical conductor may cause a maxima of the decoupling due to constructive superposition of direct and reflected waves, as shown in FIG. 2. In one or more embodiments, the maxima may be observed in the case of non-resonant conductors due to the damping. In one or more embodiments, the position of the ends of the elongated conductor may be selected such that one end of the conductor may be located within the body at a greater distance from the body surface, for example a distal end of the conductor or of the electrode line, and another end of the elongate conductor may be in contact with the active implantable medical device, for example a proximal end of the conductor or of the electrode line, in the vicinity of the body surface.

In at least one embodiment, the amplitude of the irradiated wave in the region of the distal end may be heavily reduced due to the damping in the body and therefore only contributes to a reduced extent to the amplitude of the decoupling at the electrode end, as shown in FIG. 3.

In one or more embodiments, the proximal end may be located in the vicinity of the body surface, such as in a shoulder region, and therefore may be exposed to a stronger external field.

FIG. 4 shows a prior art device with a terminal housing 104 and electrical components of a filter feedthrough of a typical cardiac pacemaker. FIG. 5, in contrast thereto, shows a schematic illustration of a cardiac pacemaker with a line extension, according to one or more embodiments of the invention, and with an electrical component 120, of which an electric length thereof corresponds to at least a quarter of a wavelength λ of electromagnetic waves in a radio frequency range.

In at least one embodiment, the medical device may include an electrically conductive housing 100, which corresponds to the housing 12 of FIG. 1. In one or more embodiments, an electrode line 102, which includes a tip electrode 106, may be connected to the housing 100. In at least one embodiment, the tip electrode 106 may form or may include an electrode pole. In one or more embodiments, the electrode pole may be connected via a feed line 110 to an electronics unit in an interior of the housing 100. In at least one embodiment, the feed line 110 may form or may include a function conductor.

In one or more embodiments, the feed line 110, such as a function conductor, may be guided via a plug (not illustrated in FIGS. 4 and 5).

As shown in the prior art device according to FIG. 4, a filter feedthrough with a terminal electronics unit 120 adjoins the plug and by the cardiac pacemaker electronics unit located in the interior of the housing 100.

The terminal electronics unit 120, of FIG. 4, generally serves to filter the signals and is formed, for example, by two series circuits, connected parallel to one another, of a coil 122 and of a capacitor 124. As shown in FIG. 4, the coil 122 and capacitor 124 are adjoined by a parallel circuit of an ohmic resistor 126 and a further capacitor 128. In the prior art device of FIG. 4, the terminal electronics unit is arranged in the terminal housing 104.

At least one embodiment of the invention, as shown in FIG. 5, may include impedance matching components 130 that may be located in the terminal housing 104. In one or more embodiments, the impedance matching components 130 may be formed by or may include an ohmic resistor 132 and a capacitor 134 connected parallel thereto. In at least one embodiment, as shown in FIG. 5, the function conductor 110, which may include a plurality of function conductors 110, may be connected via the impedance matching components 130 to the line extension 140. In one or more embodiments, the line extension 140 may include two extension conductors 142, which may be located in the housing 100 of the cardiac pacemaker. In at least one embodiment, the two extension conductors 142 may be connected at the proximal end thereof, distanced from the terminal housing 104, to a connection electronics unit 120'. In one or more embodiments, the terminal electronics unit 120', as shown in FIG. 5, corresponds to the terminal electronics unit 120 of FIG. 4, except wherein the terminal electronics unit 120' is not arranged in the terminal housing 104, but in the housing 100.

One or more embodiments may include two series circuits, which on an input side each comprise the impedance matching components 130, wherein the two series circuits may be adjoined by an extension conductor 142, which is terminated by a coil (inductor) 122' and a capacitor 124'. In at least one embodiment, the two series circuits may be connected parallel to one another, for example wherein the two capacitors 124' are connected to one another on an output side and are connected jointly to a parallel circuit including an ohmic resistor 126' and a capacitor 128'.

In one or more embodiments, the electric component 140 may include an electric length corresponding to at least a quarter of the wavelength λ of electromagnetic waves in the radio frequency range, referred to herein as a line extension.

In one or more embodiments of the invention, for example compared with a typical cardiac pacemaker as shown in FIG. 4, the terminal housing (header) of the cardiac pacemaker may be replaced by a plug connection. For example, in at least one embodiment, the plug connection may be supplemented by the impedance matching components 130 by impedance matching at the electrode line in order to minimize reflections.

In one or more embodiments, the line extension 140 within the pacemaker may include cables/wires, such as low-resistive cables/wires, that may be guided along the housing 100. As such, in at least one embodiment, the electric length of the function conductor 110 of the electrode line 102 may be extended accordingly. In one or more embodiments, the line extension 140 may correspond approximately to a double winding of the electrode line around the cardiac pacemaker. According to one or more embodiments, with an RF resonator, additional windings of electrode lines around the cardiac pacemaker may lead to a significant reduction of RF-induced heating, wherein the region of the windings may be shielded in part by the metal housing of the cardiac pacemaker. In at least one embodiment, the terminal point of the electrode line of the active implantable medical device, such as the cardiac pacemaker, may be located within the housing of the cardiac pacemaker. One or more embodiments of the invention may include a capacitive coupling of the cables/wires to the housing of the cardiac pacemaker to deliver coupled-in energy to the surrounding tissue without damaging the tissue as a result of the application of heat.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

LIST OF REFERENCE SIGNS 10 heart stimulator
12, 100 housing
14, 104 terminal housing
16 electrical contact
20, 102 electrode line
22, 106 tip electrode
24 ring electrode
26 electrical conductor
28 plug contact
30, 32 electrode pole
110 feed line
120, 120' terminal electronics unit
122, 122' coil (inductor)
124, 124' capacitor
126, 126' ohmic resistor
128, 128' additional capacitor
130 impedance matching components
132 ohmic resistor
134 capacitor
140 line extension
142 extension conductor

What is claimed is:

1. An implantable medical device comprising:
a housing;
an electrode line comprising:
  at least one elongate electrical function conductor connected to the housing and configured to transmit therapy and/or diagnostic signals; and
  at least one electrode pole connected to the at least one electrical function conductor and adapted to deliver electric current to adjacent body tissue and/or sense electrical potential of surrounding tissue; and
at least one electrical component located within the housing and having an electric length, wherein the electrical length corresponds to at least a quarter of a wavelength λ, of electromagnetic waves in a radio frequency range which occur in 1.5 Tesla or 3 Tesla Magnetic Resonance Imaging (MRI) scanners;
wherein the electrode line is electrically connected to the at least one electrical component; and
wherein the at least one electrical component is a low-resistive conductive extension wire which directly extends from the electrode line by the electric length.

2. The implantable medical device according to claim 1, wherein the housing is electrically conductive, or wherein the housing comprises the at least one electrode pole, and wherein via said housing, said electric current is configured to be delivered to the surrounding body tissue and/or said electrical potentials are configured to be sensed in the surrounding tissue.

3. The implantable medical device according to claim 1, further comprising an impedance matching component configured to impedance match between the at least one elongate electrical function conductor and the at least one electrical component such that the impedance matching component matches impedances of the at least one elongate electrical function conductor and the electrical conductive component.

4. The implantable medical device according to claim 3, wherein the impedance matching component is a spur line or comprises a spur line.

5. The implantable medical device according to claim 3, wherein the impedance matching component is a balun or comprises a balun.

6. The implantable medical device according to claim 3, wherein the impedance matching component is a capacitor or comprises a capacitor.

7. The implantable medical device according to claim 3, wherein the impedance matching component is an inductor or comprises an inductor.

8. The implantable medical device according to claim 3, wherein the impedance matching component is a combination of an inductor and a capacitor, or wherein the impedance matching component comprises a combination of an inductor and a capacitor.

9. The implantable medical device according to claim 1, wherein the at least one electrical component is insulated along a length thereof.

10. The implantable medical device according to claim 1, wherein the at least one electrical component is configured to be in contact with a medium that fully or partially includes of one or more of glass, barium titanate, polyethylene, silicon oxide, silicon carbide, ceramic, piezo materials, alumina, titanium oxide, tantalum oxide, semiconductor materials, and plastics.

11. The implantable medical device according to claim 1, wherein the low-resistive conductive extension wire comprises one or more of a wire/band, a platinum-plated wire/band, a wound wire/band, a stranded wire, a cable, a printed conductor, a cut conductor, an etched conductor, a galvanically deposited conductor, and a slitted conductive surface.

* * * * *